United States Patent [19]

Balliet

[11] 4,408,846
[45] Oct. 11, 1983

[54] METHOD AND APPARATUS FOR INCREASING VISUAL ACUITY

[75] Inventor: Richard F. Balliet, Martinez, Calif.
[73] Assignee: Andrew M. Clay, San Francisco, Calif. ; a part interest
[21] Appl. No.: 230,905
[22] Filed: Feb. 2, 1981
[51] Int. Cl.³ ............................ A61B 3/00; A61B 3/02
[52] U.S. Cl. .................................... 351/203; 351/237; 351/239; 351/243
[58] Field of Search .......................... 351/39, 2, 32–38, 351/30

[56] References Cited

U.S. PATENT DOCUMENTS 4,105,302  8/1978  Tate .................................... 351/30

Primary Examiner—John K. Corbin
Assistant Examiner—Rodney B. Bovernick
Attorney, Agent, or Firm—Robert Charles Hill

[57] ABSTRACT

A method and apparatus for increasing visual acuity of a person wherein a target is selectively moved toward or away from the person to different positions at accurately determined distances therefrom. At each of the positions, the person is required to identify the appearance of the target which is randomly changed to any one of a plurality of different appearances. The concept includes the moving of the target further away from the person whenever the identification of the target appearance is correct at a given position and moving the target closer to the person whenever the identification is incorrect. The invention comprehends moving the target incrementally at smaller distances away from the person than toward the person. A Badal lens is interposed between the person and the target for causing the focal points to be at the nodal point of the eye of the person. The target is illuminated with red light in the illustrated embodiment and is defined by line gratings wherein the different appearances of the target are provided by different diagonal line orientations. A display is provided for indicating to the user at all times the target distance and recording apparatus is provided for recording the respective distance and identifications for subsequent use in analysis of the visual training. The system is advantageously adapted for increasing the far-point acuity of a myopic person, as well as increasing the visual acuity of an emmetropic person.

30 Claims, 5 Drawing Figures

METHOD AND APPARATUS FOR INCREASING VISUAL ACUITY

BACKGROUND OF THE INVENTION

1. Field of the Invention

This invention relates to optometry and in particular to apparatus and means for improving visual acuity of persons.

2. Description of the Background Art

It has been common to provide eye training, such as a wide range of eye exercises.

Visual abilities include normal vision characteristics, such as represented by the conventional 20/20 characterization of a person that can read at 20 feet letters designed to be read at 20 feet. Additional visual abilities include the ability to follow moving objects, to fixate on a series of fixed objects, the change focus between objects at different distances, to maintain attention for extended periods of time, to judge relative distances of objects accurately, to utilize peripheral vision, and to read rapidly. One important visual ability is the far-point acuity of the person.

SUMMARY OF THE INVENTION

The present invention is concerned with an improved method and apparatus for increasing the far-point acuity of a myopic person as well as increasing the visual acuity of a normal or emmetropic person.

The invention comprehends having a person identify the appearance of a target which is caused to present selectively and randomly different appearances at different distances from the person. The target is moved incrementally toward or away from the person as a result of the person incorrectly or correctly identifying the appearance of the target at each distance.

In normal use, the far point of the person is determined and the target is firstly positioned at a preselected distance closer to the person than his normal far point. The target is then caused to present one of the randomly different appearances, and the person is asked to identify that appearance. If the person correctly identifies the appearance, the target is moved away from the person a preselected distance and the person is then again asked to identify the randomly selected appearance of the target at the new distance. If the person incorrectly identifies the appearance, the target is moved closer to the person a different preselected distance and the person is again asked to identify the randomly identified appearance at the closer distance.

In the illustrated embodiment, the target is moved away from the person a lesser distance than it is moved toward the person in each incremental change of position.

The identifications are caused to be made monocularly.

In the illustrated embodiment, the target displays randomly two mirror image appearances defining the different appearances thereof.

In the illustrated embodiment, the movement of the target toward the person is caused to be approximately three times the movement away from the person.

The invention further comprehends the step of recording the target distances and corresponding correct and incorrect identifications.

The invention comprehends the provision of a read-out display of the target distance at all times to the person during the training session.

In the illustrated embodiment, the target is illuminated with red light.

The target, in the illustrated embodiment, is transilluminated.

In the illustrated embodiment, the target is carried in an optical bench having means for incrementally moving the support of the target toward or away from the person.

The person's head may be fixed during the training session as by the provision of a bite bar gripped by the person's teeth during the training session.

In the illustrated embodiment, a positive Badal lens configuration is provided between the person and the target. In one form, the lens is +10 diopters.

In the illustrated embodiment, the target when it is a +10 diopter Badal lens configuration is defined by line gratings having 600 lines per inch so as to provide a 20/30 Snellen characteristic equal to 20 cycles per degree.

A stop aperture may be provided between the person and the target so as to provide a small visual angle field, such as approximately 3°.

Means are provided for recording the respective identifications and target distances in the use of the apparatus, and a display may be provided for indicating the target distance to the person.

BRIEF DESCRIPTION OF THE DRAWING

Other features and advantages of the invention will be apparent from the following description taken in connection with the accompanying drawing wherein.

DESCRIPTION OF THE PREFERRED EMBODIMENT

Figure 1:
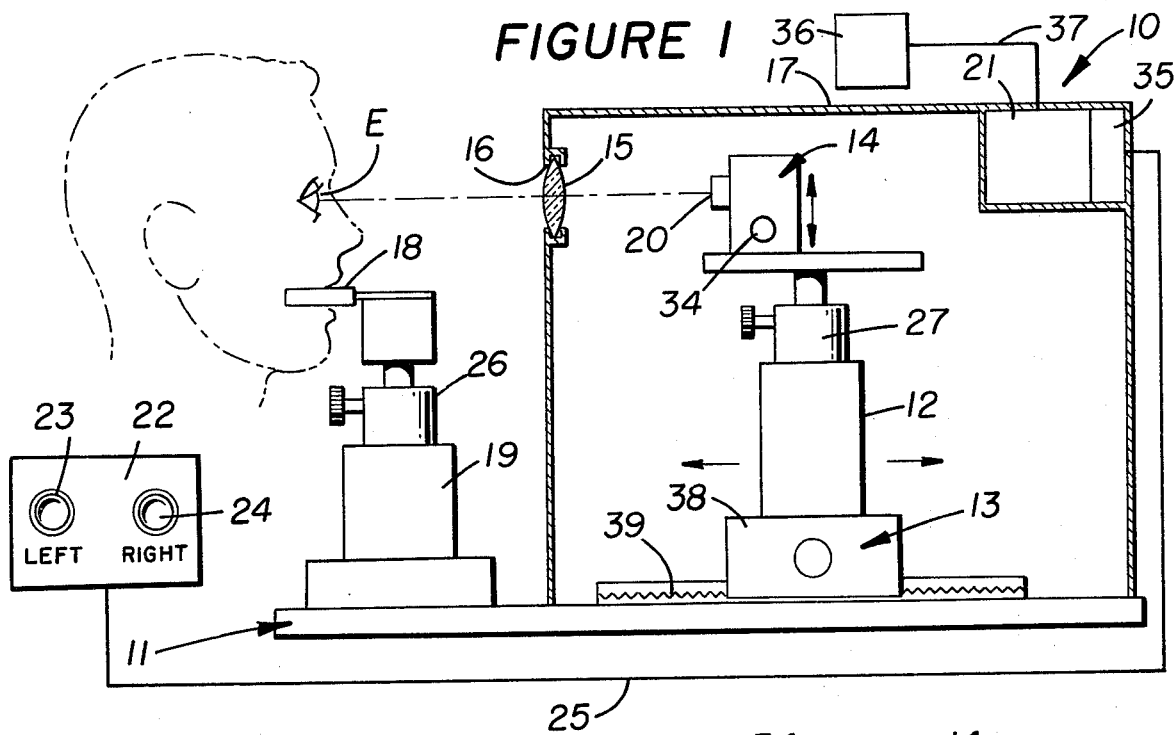
FIG. 1 is a side elevation of an apparatus for conducting a method of increasing visual acuity of a person embodying the invention.

In the exemplary embodiment of the invention as disclosed in the drawing, an apparatus generally designed 10 is provided for use in increasing the visual acuity of a person by an improved method wherein the person is repeatedly asked to identify the appearance of a target located at different distances from the person's eye. Apparatus 10 may include an optical bench 11 provided with a support 12, which is incrementally moved toward or away from the person by a stepping motor drive 13 of conventional construction. A target device generally designated 14 is carried on the support for corresponding movement toward or away from a Badal lens 15 mounted in an aperture 16 provided in a housing 17.

A bite plate 18 is carried on a support 19 to be gripped by the person's teeth so as to accurately locate his eyes E in position to view the target 20 through the lens 15. In the illustrated embodiment, bite plate 18 is located so as to dispose the nodal point of the person's eye at a distance equal to the posterior focal point of lens 15.

Likewise, the distance of target 20 rearwardly of lens 15 is equal to the anterior focal point of lens 15. A suitable control 21 is mounted in the housing for incrementally moving the support 12 by the stepping device 13 selectively toward or away from the person's eyes. A control box 22 includes a first pushbutton 23 and a second pushbutton 24 for manipulation by the person to identify which of different appearances the target presents to the person at each step in the training process. Control 22 may be connected to control 21 by a suitable electrical cable 25. Control 21 may comprise any suitable control, as will be obvious to those skilled in the art, for effecting controlled operation of the stepping motor drive 13 in either a forward or rearward direction.

As further indicated in FIG. 1, support 19 is provided with a triaxial device 26 for adjusting the position of the bite plate to locate the user's eyes E appropriately relative to the lens 15, and support 12 is provided with a similar adjustment device 27 for adjusting the target device 14 for alignment with the person's eyes E.

Figure 2:
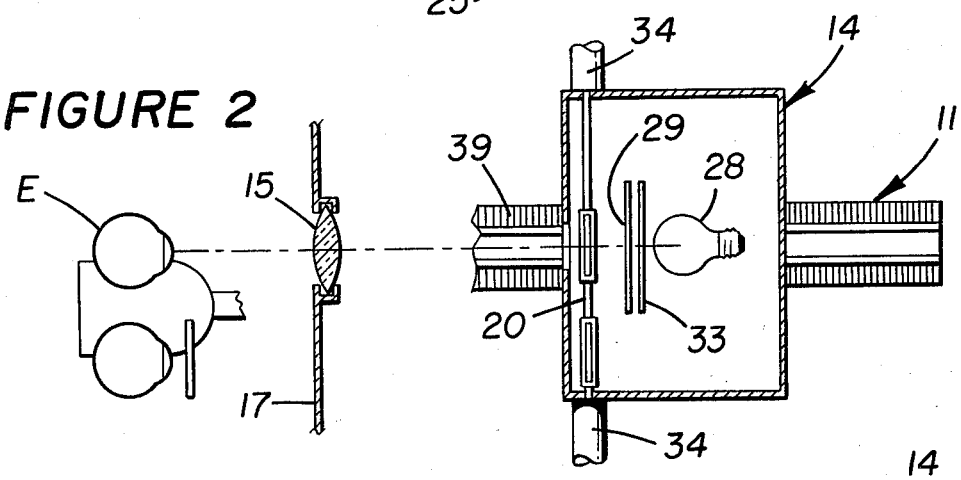
FIG. 2 is a schematic top plan view of a portion thereof.

As shown in FIG. 2, viewing of the target is done monocularly with only one of the person's eyes viewing the target through the lens 15 at a given time. As further shown in FIG. 2, the target is illuminated from an illumination source, such as a standard tungsten lamp bulb 28, with the light being passed through a suitable filter 29 to provide illumination of the target. In the illustrated embodiment, the filter comprises a #29 Wratten filter having a dominant wavelength of 632 n.m. at 1.0 ft. candle. Lens 15 may include a +0.2 diopter correction factor to equate the red light to white light.

Figure 3:
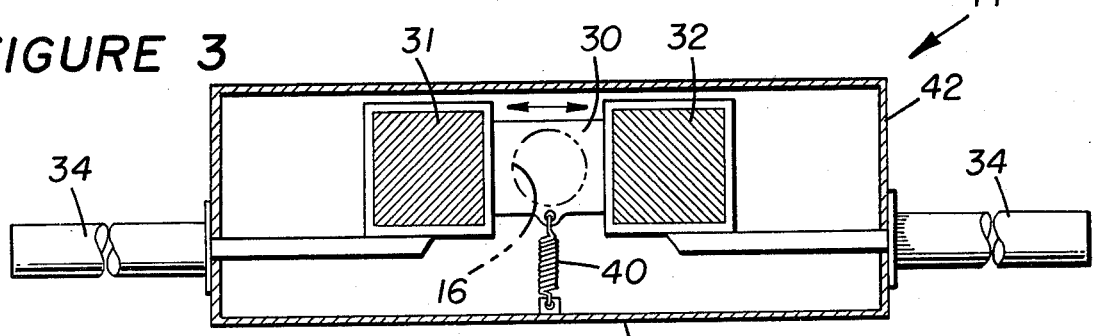
FIG. 3 is a front elevation of the target structure.
Figure 4:
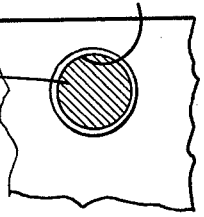
FIG. 4 is a front elevation of the target as viewed by the person presenting one of a plurality of different appearances.
Figure 5:
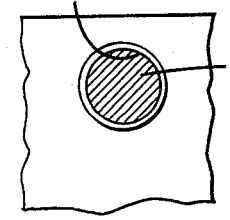
FIG. 5 is a fragmentary view similar to that of FIG. 4 illustrating the target showing a different appearance.

As shown in FIGS. 2 and 3, target 20 comprises a support plate 30 carrying at its opposite sides two target transparencies 31 and 32 having different appearances. In the illustrated embodiment, the target transparencies comprise diagonally oriented, square wave gratings with the lines of grating 31 angled at 45° and the lines of grating 32 angled at 315°. Each of the gratings is equal to 20 cycles per degree (20/30 Snellen) and as shown in FIG. 4, are viewed by the person through aperture 16, which defines a 3° visual angle field stop aperture.

Light from bulb 28 is defused by a suitable defusion screen 33 which, in the illustrated embodiment, comprises a translucent white Mylar sheet. Thus, as seen in FIG. 4, the target elements 31 and 32 are uniformly illuminated for identification by the person when presented for viewing through the aperture 16.

The transparency elements 31 and 32 are selectively positioned for viewing through aperture 16 by movement of the target support plate 30 to the left or to the right, as seen in FIG. 3, so as to selectively dispose either of the gratings 31 or 32 in alignment with the aperture 16 in a random fashion. Controls for providing such random selection are well known in the computer art, and in the illustrated embodiment, control 21 includes an Apple II computer which is programmed to present either of the two stimuli, i.e. targets 31 or 32 randomly for viewing through the aperture 16. The computer may, in conventional fashion, selectively control the stepping motor drive 13 as a function of the correctness or incorrectness of the previous identification and further may record all of the parameters at each step of the training process for subsequent analysis.

In the illustrated embodiment, the target support plate is selectively positioned in a middle, nondisplay position, as shown in FIG. 3, and is moved to either of the display positions wherein grating 31 is aligned with aperture 16 or grating 32 is aligned therewith by suitable conventional solenoid means schematically illustrated at 34 in FIG. 3.

Control 21 may include conventional printing means 35 for providing a printout of the recorded information.

A display 36 may be provided for displaying at all times to the person the position of the target. As shown in FIG. 1, the display may be suitably connected to control 21 by a control cable 37.

Stepping motor drive 13 may include a geared carrier 38 cooperating with a rack 39 on the optical bench for accurately positioning the target 20 during the training process. In one embodiment of the invention, the stepping motor drive 13 is arranged to provide stepped movements in increments of 0.065 mm with an accuracy of ±0.01 mm.

Thus, apparatus 10 effectively comprises an optometer which is utilized in a visual feedback manner so as to extend the far-point acuity ability of a myopic person and increase the visual acuity of an emmetropic or normal person. The invention comprehends the method of increasing such visual acuity, including the steps of determining the far point of the person's visual acuity, providing a target having randomly different appearances, each of which can be identified by a person when positioned at an effective optical distance from the person equal to the person's far point, positioning the target at a first position closer to the person than the far point, with the target randomly displaying one of the appearances for identification by the person, moving the target away from the person to a second position further from the person than the first position in the event the identification of the target appearance at the first position was correct, or alternatively moving the target toward the person to a third position closer to the person than the first position in the event the identification of the target appearance at the first position was incorrect, and repeating such alternative movement of the target alternatively away or toward from the person to new positions in accordance with the correctness or incorrectness of the identifications at each new position.

The illustrated embodiment of the apparatus for carrying out such a method broadly includes means defining a target having randomly different appearances, each of which can be identified by a person when positioned at an effective optical distance from the person equal to the person's far point, means positioning the target at a first position closer to the person than the far point, means for randomly causing one of the target appearances to be displayed at the first position for identification by the person, means for moving the target away from the person to a second position further from the person than the first position in the event the identification of the target appearance at the first position was correct, or alternatively moving the target toward the person to a third position closer to the person than the first position in the event the identification of the target appearance at the first position was incorrect, and repeating such alternative movement of the target alternatively toward or from the person to new positions in accordance with the correctness or incorrectness of the identifications at each new position.

It has been found advantageous to assure that the person being trained is comfortable and relaxed. It has further been found desirable to carry out the training in a dark room, permitting the subject to more readily concentrate on the target stimulus.

The training of the person is initiated by arranging the target at a position somewhat closer than the person's predetermined far-point distance. The person is then asked to identify which of the two target appearances is presented by the random selection effected by control 22. The person may make his identification by pressing either button 23 or 24. Control 21 ascertains whether the person's identification is correct or incorrect. If the identification is correct, control 21 causes operation of the stepping motor drive 13 to move the target further away from the person by 0.10 diopters. The person is then again asked to identify the target which again is randomly selected at the new position. If the person makes an incorrect identification, the control causes a movement of the target closer to the person by a distance equivalent to 0.3 diopters. Thus, the movement effected by a correct identification away from the person is caused to be substantially lesser than the movement toward the person so as to maintain an approximately 75 to 82% correct criterion wherein incorrect responses are kept to a minimum, thereby providing optimal psychophysical motivation in the training process.

During the training session, the display 36, which may comprise a conventional TV monitor, provides a readout of the target distance at all times to the person. As discussed above, during the training, all of the information as to target distances and identifications may be stored in the control 21 and upon completion of the training session, the information printed out by printer 35 with mean and standard deviations computed in the printout. Such printout calculations may further be displayed on display device 36 for review by the person.

The use of the training method herein has been carried out in efficacious manner by being conducted in sessions of approximately 45 minutes per day, five days a week, for periods up to four months.

In order to prevent the person from obtaining any information as to the target selection, the target support plate 30 may be biased to the midposition by a suitable spring 40, and moved to either of the randomly selected target positions by the solenoids 34. As shown in FIG. 3, spring 40 has one end secured to the bottom wall 41 of a housing 42 enclosing the target device 14. The other end of spring 40 is connected to the plate 30. Since the computer first briefly puts out no signal to either solenoid 34, spring 40 biases target 20 to the center disposition of FIG. 3. Then the computer randomly puts a signal to one of the solenoids effecting random target selection. Resultingly, the same type of movement operation and production of sound occurs in the selection of either of the targets 31 or 32, thus preventing any clue as to the selected target by audio or tactile vibrations transmitted to the person, thereby effectively minimizing cheating by the person.

The improvement in far-point acuity has been found advantageous in cases of myopia, where the person has a reduced far point. The object of such training is to increase the far-point acuity to at least 20/20 acuity level, which is a conventionally accepted definition of good acuity.

It has been found for the emmetropic (normal) person particularly in dim light, the optimal visual acuity is usually found to be within a range of approximately three to six feet. Thus, the method and apparatus of the present invention, in extending such a person's acuity to greater distances, provides substantial improvement in the normal person's overall seeing ability. Such improvement is highly efficacious for persons involved in activities, such as applied to athletics. For example, a baseball player by using this method and apparatus could extend the distance at which he sees the spin of a pitched ball, thereby allowing him to more effectively adjust his swing to a particular pitch.

By means of the Badal lens systems, the target always remains the same size, although the effective distance from the person varies. Further, the target brightness and color will be the same for all positions as a result of the use of the Badal lens system. Therefore, the target effectively has the same identity over the entire range of positioning. The use of the red light in transilluminating the target obviates the need for dark adaptation of the person.

In the present embodiment with lens 15 being a 10 diopter Badal lens, the nodal point of the eye is 10.2 cm from the lens 15, which distance is the posterior focal point of the lens 15. 10 cm are necessary because of the 10 diopter lens and 0.2 cm are necessary as a correction factor to equate red light to white light. Also each 1 cm movement of the target toward or away from the person equals to 1.02 diopter. Thus, a 1 mm movement equals 0.102 diopter and a 3 mm movement equals 0.306 diopter.

The foregoing disclosure of specific embodiments is illustrative of the broad inventive concepts comprehended by the invention.

I claim:

1. The method of increasing visual acuity of a myopic person, comprising the steps of:
   determining the far point of the myopic person's visual acuity;
   providing a target having randomly different appearances each of which can be identified by a person when positioned at an effective optical distance from the person equal to said person's far point;
   positioning the target at a first position closer to the person than said far point with the target randomly displaying one of said appearances for identification by said person
   moving the target away from the person to a second position further from the person than said first position in the event the identification of the target appearance at said first position was correct, or alternatively moving the target toward the person to a third position closer to the person than said first position in the event the identification of the target appearance at said first position was incorrect; and
   repeating such alternative movement of the target alternatively toward or from the person to new positions in accordance with the correctness or incorrectness of the identifications at each new position.

2. The method of increasing visual acuity of an emmetropic person to a greater distance, comprising the steps of:
   determining the far point of the emmetropic person's visual acuity;
   providing a target having randomly different appearances each of which can be identified by a person when positioned at an effective optical distance from the person equal to said person's far point;
   positioning the target at a first position closer to the person than said far point with the target randomly displaying one of said appearances for identification by said person
   moving the target away from the person to a second position further from the person than said first position in the event the identification of the target appearance at said first position was correct, or alternatively moving the target toward the person to a third position closer to the person than said first position in the event the identification of the target appearance at said first position was incorrect; and repeating such alternative movement of the target alternatively toward or from the person to new positions in accordance with the correctness or incorrectness of the identifications at each new position.

3. The method of increasing visual acuity of claims 1 or 2 wherein said identifications are caused to be made monocularly by said person.

4. The method of increasing visual acuity of claims 1 or 2 wherein said target displays two mirror image appearances.

5. The method of increasing visual acuity of claims 1 or 2 wherein the movement of the target toward said person pursuant to an incorrect identification is larger than the movement away from said person pursuant to a correct identification.

6. The method of increasing visual acuity of claims 1 or 2 wherein the movement of the target toward said person pursuant to an incorrect identification is at least approximately three times larger than the movement away from said person pursuant to a correct identification.

7. The method of increasing visual acuity of claims 1 or 2 wherein the target is moved approximately 0.10 diopter away from said person pursuant to a correct identification.

8. The method of increasing visual acuity of claims 1 or 2 wherein the target is moved approximately 0.30 diopter toward said person pursuant to an incorrect identification.

9. The method of increasing visual acuity of claims 1 or 2 including the further step of recording the target distances and corresponding correct and incorrect identifications for further analysis.

10. The method of increasing visual acuity of claims 1 or 2 including the further step of recording the target distances and corresponding correct and incorrect identifications for further analysis and provision of mean and standard deviation computation based thereon.

11. The method of increasing visual acuity of claims 1 or 2 including the provision of a readout display of the target distance at all times to the person.

12. The method of increasing visual acuity of claims 1 or 2 wherein the target is illuminated with red light.

13. Apparatus for increasing visual acuity of a person having a determined far point, comprising:

means defining a target having randomly different appearances each of which can be identified by a person when positioned at an effective optical distance from the person equal to said person's far point;

means for positioning the target at a first position closer to the person than said far point;

means for randomly causing one of said target appearances to be displayed at said first position for identification by the person;

means for moving the target away from the person to a second position further from the person than said first position in the event the identification of the target appearance at said first position was correct, or alternatively moving the target toward the person to a third position closer to the person than said first position in the event the identification of the target appearance at said first position was incorrect, and repeating such alternative movement of the target alternatively toward or from the person to new positions in accordance with the correctness or incorrectness of the identifications at each new position.

14. The apparatus of claim 13 wherein said means for positioning the target comprises a support and means for incrementally moving the support toward or away from the person.

15. The apparatus of claim 13 including means for fixing the nodal point of the person's eye in a preselected position adjacent said target.

16. The apparatus of claim 13 including a bite bar for fixing the nodal point of a person's eye in a preselected position adjacent said target.

17. The apparatus of claim 13 wherein said means for positioning the target comprises an optical bench-like device having a support and means for incrementally moving the support toward or away from the person.

18. The apparatus of claim 13 wherein said target comprises gratings.

19. The apparatus of claim 13 wherein said target comprises gratings equal to 20 cycles per degree.

20. The apparatus of claim 13 wherein a stop aperture is positioned between the person and the target, said stop aperture having small visual angle field such as approximately 3°.

21. The apparatus of claim 13 wherein means are provided for illuminating said target.

22. The apparatus of claim 13 wherein means are provided for illuminating said target with red light.

23. The apparatus of claim 13 wherein means are provided for transilluminating said target with red light having a 632 n.m. dominant wavelength.

24. The apparatus of claim 13 wherein a positive lens is positioned for viewing of the target therethrough by said person.

25. The apparatus of claim 13 wherein a +10 diopter lens is positioned for viewing of the target by said person.

26. The apparatus of claim 13 further including means for recording the respective identifications made by the person and corresponding target distances in the use of the apparatus.

27. The apparatus of claim 13 further including a display indicating the target distance to the person.

28. The apparatus of claim 13 wherein said positioning means comprises means for causing the movement of the target away from said person pursuant to a correct identification to be smaller than the movement toward said person pursuant to an incorrect identification.

29. The apparatus of claim 13 wherein said positioning means comprises means for causing the movement of the target away from said person pursuant to a correct identification to be at least approximately three times smaller than the movement toward said person pursuant to an incorrect identification.

30. The apparatus of claim 13 wherein a Badal lens is positioned for viewing of the target by said person.

* * * * *